(12) United States Patent
Belliard et al.

(10) Patent No.: US 8,221,464 B2
(45) Date of Patent: Jul. 17, 2012

(54) DEVICE FOR CLAMPING TWO PORTIONS OF A BRAID AND AN INTERVERTEBRAL IMPLANT COMPRISING A SPACER, A BRAID, AND SUCH A CLAMPING DEVICE

(75) Inventors: Karl Pierre Belliard, La Membrolle sur Longuenee (FR); Richard Minfelde, Paris (FR)

(73) Assignee: Zimmer Spine, S.A.S., Bordeaux (FR)

( * ) Notice: Subject to any disclaimer, the term of this patent is extended or adjusted under 35 U.S.C. 154(b) by 201 days.

(21) Appl. No.: 12/679,996

(22) PCT Filed: Sep. 24, 2008

(86) PCT No.: PCT/EP2008/062791
§ 371 (c)(1),
(2), (4) Date: Mar. 25, 2010

(87) PCT Pub. No.: WO2009/040380
PCT Pub. Date: Apr. 2, 2009

(65) Prior Publication Data
US 2010/0211102 A1 Aug. 19, 2010

(30) Foreign Application Priority Data
Sep. 25, 2007 (FR) ...................................... 07 57814

(51) Int. Cl.
*A61B 17/70* (2006.01)
(52) U.S. Cl. ........................................ 606/249; 606/248
(58) Field of Classification Search .................. 606/246, 606/248, 249, 263, 151; 623/17.11–17.16
See application file for complete search history.

(56) References Cited

U.S. PATENT DOCUMENTS
902,040 A 10/1908 Wychoff
(Continued)

FOREIGN PATENT DOCUMENTS
DE 19716504 A1 12/1998
(Continued)

OTHER PUBLICATIONS
European Search Report for EP 08305124.3, dated Oct. 10, 2008, 3 pages.
(Continued)

*Primary Examiner* — Eduardo C Robert
*Assistant Examiner* — Christina Negrelli
(74) *Attorney, Agent, or Firm* — Seager Tufte & Wickhem LLC

(57) ABSTRACT

The invention relates to an intervertebral implant comprising: a spacer (12); a braid (14) for fixing said spacer between the spinous processes of two adjacent vertebrae; and a clamping device for clamping said braid. The clamping device comprises: a fixed part (28) constituted by a portion of said spacer (12) and defining at least one first clamping surface for clamping said braid; a mobile assembly (28) movable relative to said spacer (12) and defining at least one second clamping surface for clamping said braid; and displacement means for moving said moving assembly (30) relative to said fixed part (28) to displace said mobile assembly between a first position in which said first and second clamping surfaces face each other but are apart to define a free passage for a portion of the braid (14), and a second position in which said first and second clamping surfaces are moved towards each other to clamp said portion of braid (14).

18 Claims, 6 Drawing Sheets

U.S. PATENT DOCUMENTS

| | | | |
|---|---|---|---|
| 1,346,940 | A | 7/1920 | Collins |
| 2,049,361 | A | 7/1936 | Ericsson |
| 5,609,634 | A | 3/1997 | Voydeville |
| 5,667,508 | A | 9/1997 | Errico |
| 5,935,133 | A | 8/1999 | Wagner et al. |
| 5,938,663 | A | 8/1999 | Petreto |
| 5,964,769 | A | 10/1999 | Wagner et al. |
| 6,053,921 | A | 4/2000 | Wagner et al. |
| 6,086,590 | A | 7/2000 | Margulies et al. |
| 6,099,527 | A | 8/2000 | Hochschuler et al. |
| 6,179,838 | B1 | 1/2001 | Fiz |
| 6,302,889 | B1 * | 10/2001 | Keller ............................ 606/74 |
| 6,391,030 | B1 | 5/2002 | Wagner et al. |
| 6,478,798 | B1 | 11/2002 | Howland |
| 6,547,770 | B2 | 4/2003 | Carlsson et al. |
| 6,569,164 | B1 | 5/2003 | Assaker et al. |
| 6,616,669 | B2 | 9/2003 | Ogilvie et al. |
| 6,682,533 | B1 | 1/2004 | Dinsdale et al. |
| 6,946,000 | B2 | 9/2005 | Senegas et al. |
| 7,087,083 | B2 * | 8/2006 | Pasquet et al. ............. 623/17.11 |
| 7,862,592 | B2 * | 1/2011 | Peterson et al. ............. 606/249 |
| 7,909,853 | B2 * | 3/2011 | Zucherman et al. .......... 606/249 |
| 2002/0116013 | A1 | 8/2002 | Gleason et al. |
| 2004/0097942 | A1 | 5/2004 | Allen et al. |
| 2005/0273983 | A1 | 12/2005 | Mattchen |
| 2006/0235387 | A1 | 10/2006 | Peterman |
| 2008/0033557 | A1 | 2/2008 | Pasquet et al. |

FOREIGN PATENT DOCUMENTS

| | | |
|---|---|---|
| FR | 522040 | 7/1921 |
| FR | 26156 | 9/1932 |
| FR | 2704745 A1 | 11/1994 |
| FR | 2722088 A1 | 1/1996 |
| FR | 2799948 A1 | 4/2001 |
| FR | 2897771 | 8/2007 |
| WO | WO02071960 A1 | 9/2002 |
| WO | WO 03007829 A1 | 1/2003 |
| WO | WO 2005020860 A3 | 3/2005 |
| WO | WO2005120277 A1 | 12/2005 |
| WO | WO2006034423 | 3/2006 |
| WO | WO 2006106268 A3 | 10/2006 |
| WO | WO 2006106246 A2 | 12/2006 |
| WO | WO 2007023240 A3 | 3/2007 |
| WO | WO2007099258 A2 | 9/2007 |
| WO | WO2009130276 A1 | 10/2009 |
| WO | WO2009141393 A1 | 11/2009 |

OTHER PUBLICATIONS

European Search Report for EP 08305183, dated Mar. 19, 2009, 10 pages.

International Preliminary Report on Patentability issued in International Patent Application No. PCT/EP2008/062791, Mar. 30, 2010, 7 pages.

French Preliminary Search Report in French Patent Application No. FR 0405611, dated Jan. 12, 2005, 2 pages.

International Search Report and Written Opinion for PCT Application No. PCT/EP2008/062791, completed Nov. 18, 2008, mailed Dec. 4, 2008, 10 pgs.

French Preliminary Search Report for French Application No. 0757814, issued May 22, 2008, 2 pgs.

* cited by examiner

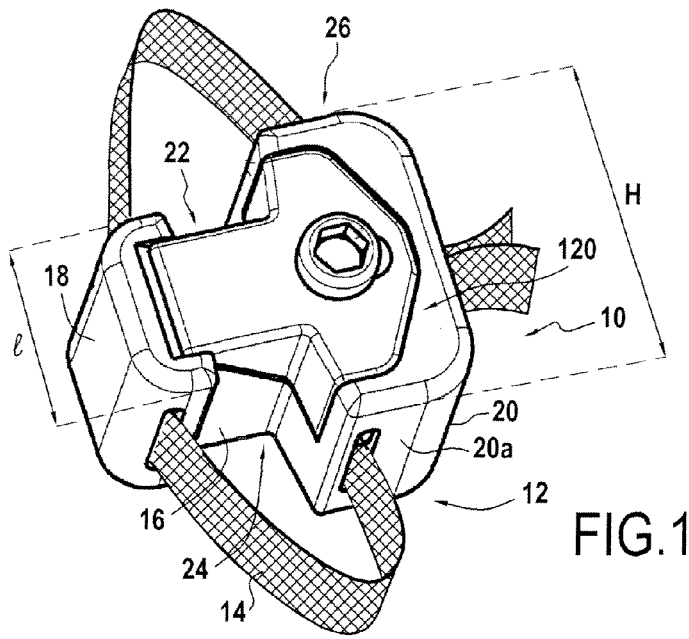
FIG.1
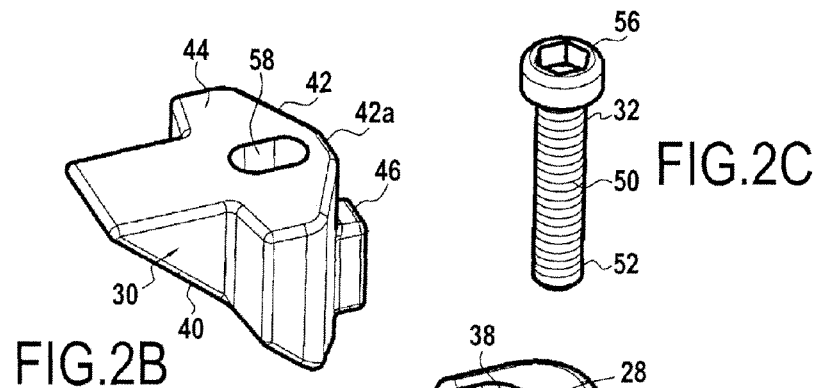
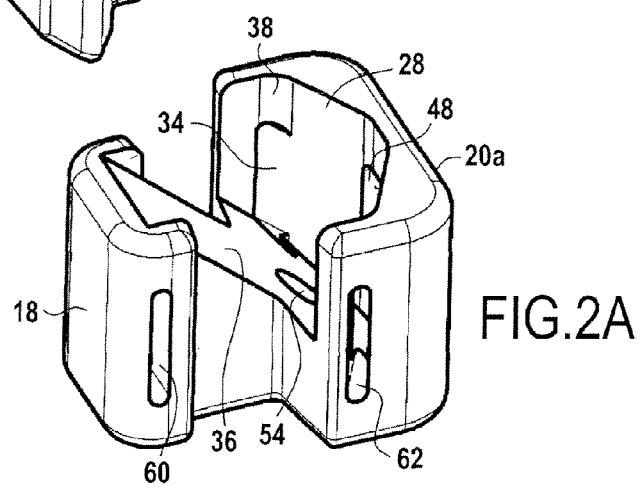
FIG.2C
FIG.2B
FIG.2A

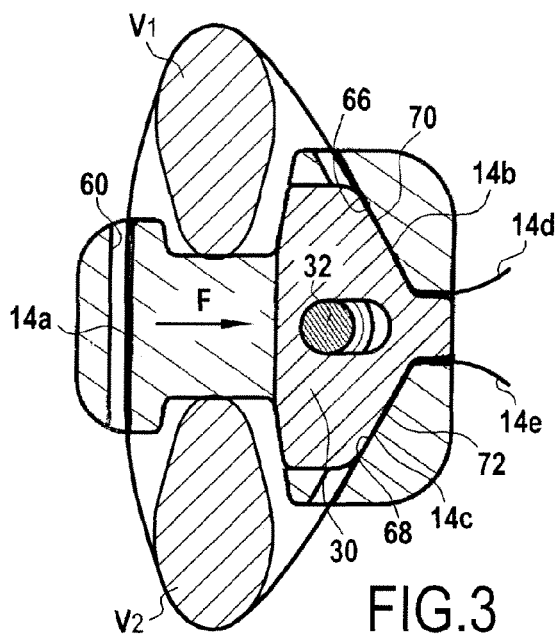
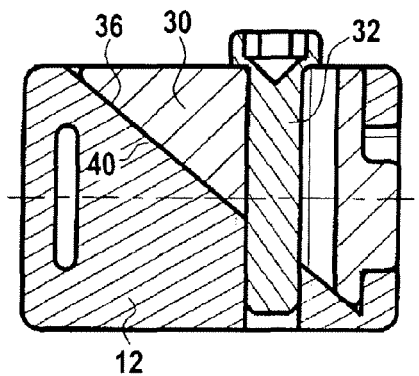
FIG.3  FIG.4
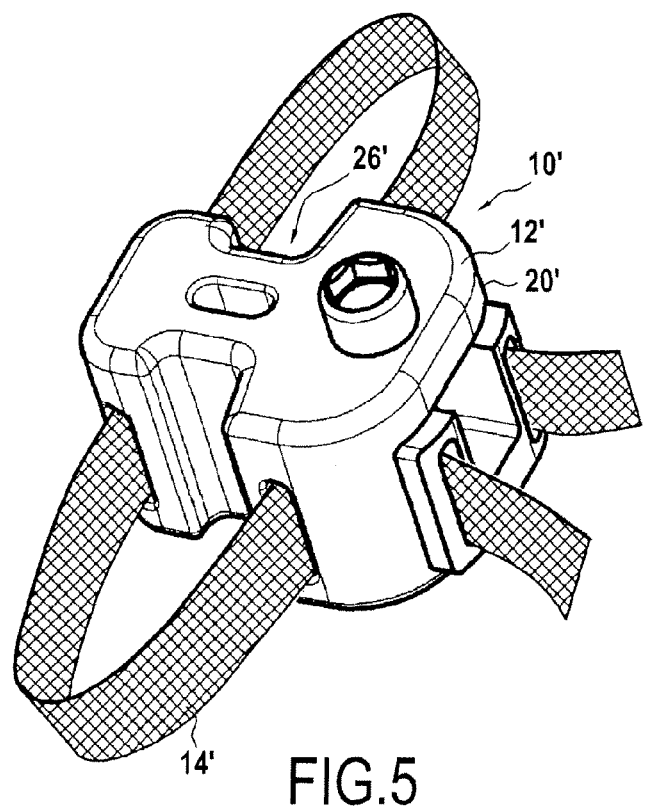
FIG.5

DEVICE FOR CLAMPING TWO PORTIONS OF A BRAID AND AN INTERVERTEBRAL IMPLANT COMPRISING A SPACER, A BRAID, AND SUCH A CLAMPING DEVICE

CROSS-REFERENCE TO RELATED APPLICATIONS

This is a national stage application of and claims priority from International Application No. PCT/EP2008/062791, filed Sep. 24, 2008, entitled "A DEVICE FOR CLAMPING TWO PORTIONS OF A BRAID AND AN INTERVERTEBRAL IMPLANT COMPRISING A SPACER, A BRAID, AND SUCH A CLAMPING DEVICE," which claims priority from French Application No. FR0757814, filed Sep. 25, 2007, entitled "Dispositif de serrage de deux portions d'une tresse," both of which are fully incorporated herein by reference.

The present invention relates to an intervertebral implant fitted with a device for clamping a braid, and more particularly, but exclusively to a lateral approach intervertebral implant, i.e. one that can be inserted between the spinous processes of two consecutive vertebrae in a lateral direction relative to the plane defined by the spine of the patient to whom the implant is to be fitted.

Implants including intervertebral spacers are described in particular in French Patent Application 2 822 051 and in French Patent Application 2 870 106 in the name of the Applicant.

Fitting that kind of spacer gives rise to certain problems linked to the surgical procedure. A ligament called the supra spinous ligament connects together all the tops of the spinous processes. To fit the spacer, this ligament must be moved. In practice, it is detached from the two spinous processes concerned and moved aside by means of an appropriate surgical instrument. A scalpel is used to detach the ligament from the spinous processes. Once the spacer is in place, the ligament is re-sutured to the spinous processes after making a small hole therein to receive the suture. The ligament can even be sectioned, if appropriate.

The major drawback of that surgical procedure is that touching the ligament to detach it and move it aside causes it to lose its mechanical properties. Moreover, all these actions take time and increase the overall duration of the surgical procedure.

When it is necessary to proceed to total ablation of the natural intervertebral disc, it is usually necessary to obtain axial access to the disc and the surgical procedure described above can therefore not be avoided.

However, there are circumstances in which the situation is different. This applies when it is necessary to proceed with the ablation of a herniated disk, which procedure requires access to only one side of the spinous body, and it is then therefore particularly beneficial to use an intervertebral implant in which the spacer can be easily fitted between the spinous processes by a lateral route since the surgical procedure as such itself requires only this access route.

This is not possible with the spacers of known intervertebral implants because the projections on either side of the housing adapted to receive the spinous process are relatively tall, typically at least 5 mm high. Such a projection height would impose vertebral distraction of the two vertebrae concerned, which would be unacceptable.

The Applicant has filed French Patent Application 2 897 771, which relates to an intervertebral implant intended to solve this problem because its spacer can be inserted laterally, in particular because the distal projection of the spacer is of small height, no more than 3 mm.

As is known in the art, the intervertebral spacer is held in place by ties or braids that pass around the spinous processes of the two adjacent vertebrae and that must be attached to the spacer itself. Moreover, these braids must have sufficient tension to ensure effective fastening of the spacer between the two vertebrae.

To clamp the braid relative to the spacer of the intervertebral implant, and thus to secure the implant to the vertebrae, it is known to associate a double self-locking system with the body of the spacer, which system is clipped onto the spacer body by the surgeon. Such a braid clamping system is described in particular in above-mentioned French patent application 2 897 771.

That braid clamping system is effective, however it requires the surgeon to clip the self-locking system onto the body of the spacer.

An object of the present invention is to provide an intervertebral implant, in particular for lateral insertion, that is associated with a braid clamping device that can be actuated and installed in simplified manner by the surgeon.

According to the invention, the intervertebral implant comprises: a spacer; a braid for fixing said spacer between the spinous processes of two adjacent vertebrae; and a device for clamping said braid.

The clamping device comprises:
- a fixed part constituted by a portion of said spacer and defining at least a first clamping surface for clamping said braid;
- a mobile assembly that is mobile relative to said spacer, defining at least a second clamping surface for clamping said braid; and
- displacement means for moving said mobile assembly relative to said fixed part to move said mobile assembly between a first position in which said first and second clamping surfaces face each other but are apart to define a free passage for a portion of the braid and a second position in which said first and second clamping surfaces are moved towards each other to clamp said braid portion, said displacement means being further adapted to hold said mobile assembly in its clamping, second position.

It will be understood that since the fixed part of the braid clamping device is constituted by a portion of the spacer of the implant, putting the intervertebral implant into place with its braid clamping device is greatly simplified, as is tightening the braid.

Preferably, the fixed first part of the clamping device forms an integral portion of the spacer and is fabricated in any appropriate manner at the same time as the spacer.

Also preferably, said spacer comprises a middle portion and two end portions, respectively a proximal end portion and a distal portion, extending orthogonally relative to the direction in which said spacer is inserted between the vertebrae, said spacer having two recesses disposed respectively at two ends of said median portion between the ends of said end portions, the proximal end portion defining at least a portion of said fixed part of the clamping device.

According to a preferred characteristic, the distal second end portion of the spacer includes a passage in which a median portion of said braid is engaged freely.

Also preferably, the spacer is configured to enable lateral insertion.

In a preferred embodiment, said fixed part defines two distinct first clamping surfaces, and said mobile assembly defines two distinct second clamping surfaces, thereby enabling two distinct portions of the braid to be clamped.

Clearly, because two braid clamping areas corresponding to two separate portions of the braid are defined by the clamping surfaces of the two members, only one end of the braid needs to be fastened to the spacer permanently or, more generally, fastened to the system on which the clamping device is mounted.

Furthermore, because the clamping device operates on two separate portions of the braid, this leaves both ends of the braid free, enabling appropriate traction to be applied to the braid as a whole, whatever the risks that may exist of friction between the system on which the clamping device is mounted and the braid itself.

In a first embodiment of the invention, the clamping device is characterized in that said mobile assembly consists of a single second part.

Clearly, the clamping and therefore the immobilization of the two portions of the braid are then effected simultaneously.

In a first mode of use of the first embodiment of the clamping device, said displacement means comprise a first sliding face of said first part inclined relative to the direction of movement and a second sliding face of said second part adapted to co-operate with said first sliding face, said second sliding face also being inclined relative to the direction of movement, and a mechanical member for causing the second sliding face to slide relative to the first sliding face between said first and second positions.

In this mode of use, the clamping device is preferably characterized in that said mechanical member is a screw with a threaded end that co-operates with tapping formed in the inclined face of the first part, the shank that passes through an oblong aperture in said second part, and a head that is in contact with a face of said second part opposite its inclined face.

Alternatively, the opposite arrangement can be used, i.e. the screw can be mounted in the second part and the head of the screw can co-operate with the first part.

In a second mode of use of the first embodiment of the invention, the clamping device is characterized in that said displacement means comprise respective sliding faces on each of said parts parallel to the direction of movement and adapted to co-operate mutually, and a mechanical displacement member.

In this second mode of use of the invention, the clamping device is preferably characterized in that said displacement member has an inclined surface on said second part opposite the sliding face and a screw engaged in tapping formed in said first part and having one end that co-operates with said inclined surface.

In a variant of the second mode of use, the displacement member comprises a screwing member of axis parallel to the direction of movement, the head of said screwing member bears on an external face of said mobile second part, and the threaded portion of the screwing member co-operates with tapping formed in said first part.

In a second embodiment of the invention, the clamping device is characterized in that said mobile assembly comprises two separate second parts that are separately mobile, each second part defining one of the two second clamping surfaces.

Clearly, in this embodiment, each braid portion can be clamped separately. The surgeon can therefore fix the braid to each of the spinous processes in succession.

In this embodiment, the clamping device is preferably characterized in that said first part has a first sliding face and each mobile second part has a second sliding face, said two second sliding faces being adapted to co-operate with said first sliding face, and in that it further comprises two mechanical members for causing the second sliding face of each mobile second part to slide separately relative to the first sliding face of said first part between said first and second positions.

Whichever mode of use is considered, the clamping surfaces can consist of surfaces that are movable relative to each other and that are inclined to the direction of movement of one assembly relative to the other. At least one of the clamping surfaces can be an edge facing a second clamping surface that is plane. The clamping surfaces can further include notches, lugs, and/or asperities.

Other, features and advantages of the invention become more clearly apparent on reading the following description of embodiments of the invention given by way of non-limiting example. The description refers to the appended drawings, in which:

FIG. 1 is a perspective view of a lateral approach intervertebral spacer equipped with a first embodiment of the braid clamping device;

FIG. 2A shows in perspective the portion of the intervertebral spacer forming the first part of the FIG. 1 clamping device;

FIG. 2B shows in perspective the second part of the FIG. 1 clamping device;

FIG. 2C shows in perspective the mechanical member of the FIG. 1 clamping device;

FIG. 3 is a view in section on a plane H-H in FIG. 1 showing how the braid co-operates with the spinous processes;

FIG. 4 is a view in vertical section on the plane V-V in FIG. 1;

FIG. 5 is a perspective view of a spacer of an intervertebral implant equipped with a second mode of use of the first embodiment of the braid clamping device;

Figure 6:
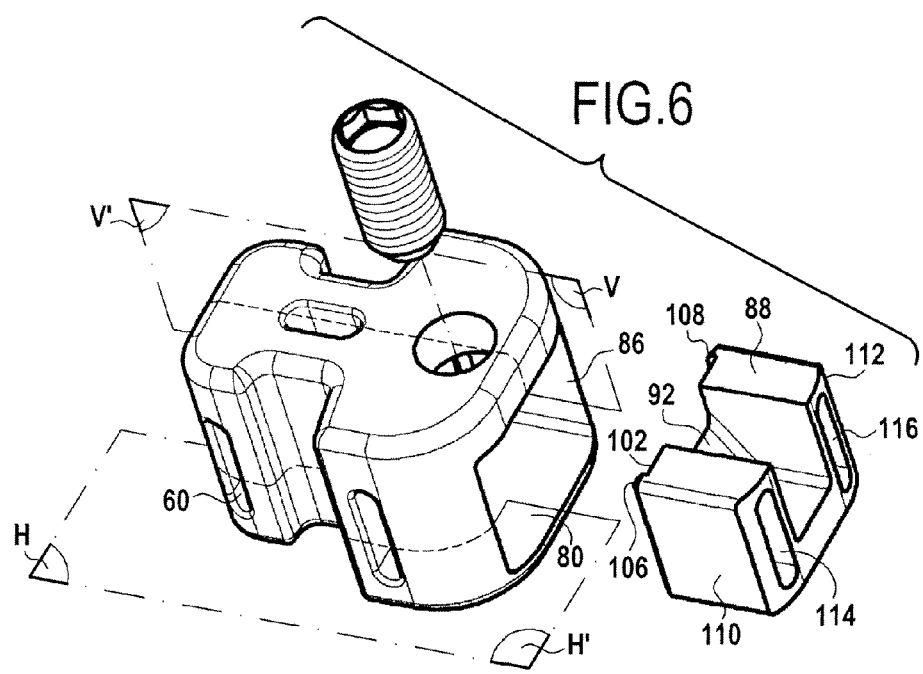
FIG. 6 shows the various components of the second mode of use of the clamping device.

The following description more particularly describes preferred embodiments of the invention, in which the intervertebral spacers are for a lateral approach and are equipped with devices for clamping two portions of a braid.

Referring first of all to FIGS. 1 to 4, an embodiment of an intervertebral implant equipped with a first mode of use of a first embodiment of the braid clamping device is described first with reference to FIGS. 1 to 4.

In the first embodiment of the clamping device, the two braid portions are clamped simultaneously.

The intervertebral implant 10 essentially consists of a spacer 12 and a flexible deformable braid 14 for fixing the spacer between the spinous processes of the vertebrae.

As is well known in the art, the spacer body 12 comprises a median portion 16, a distal portion 18, and a proximal end portion 20. The end portions 18 and 20 are longer than the median portion 16 to define at each end of the median portion notches or recesses 22 and 24 adapted to receive the spinous processes. As can be seen, the spacer being intended to form part of a lateral approach implant, the length l of the distal end portion 18 is less than the length L of the proximal end portion 20. In the present text, the word "distal" refers to the end of the implant farthest from the surgeon while the surgeon is inserting it, the word "proximal" referring to the other end.

To enable clamping of two portions of the braid 14, the spacer 12 is equipped with a clamping device 26 that consists of a fixed first part 28 that comprises the proximal portion 20, the median portion 16, a mobile portion 30, and, finally, a mechanical displacement member 32.

Thus in this embodiment, the fixed part of the clamping device forms an integral portion of the spacer and can be fabricated at the same time as the spacer.

A recess 34 is formed in the proximal end portion 20, the median portion 16 and a small portion of the distal end portion 18. This recess is defined by an inclined bottom wall 36 and essentially by a lateral wall 38 that is substantially parallel to the external wall 20a of the proximal portion 20.

The mobile part 30 of the clamping system has a lower face 40, a lateral face 42 conjugate with the lateral face 38 of the recess 34, and a substantially plane upper face 44. The part 30 is of course adapted to be placed in the housing 34, its inclined lower face 40 resting on the inclined face 36 of the housing 34 to constitute two sliding faces. Moreover, the end 42a of the part 30 has an extension 46 that can enter an opening 48 passing through the proximal end 20 of the spacer body.

A mechanical member 32 is provided for driving movement of the mobile part 30 consisting of the spacer body relative to the fixed part 28. It preferably consists of a screw 50 having an end 52 that co-operates with tapping 54 formed in the inclined face 36 of the housing 34 and a head 56 that bears on the upper face 44 of the mobile part 30. Finally, the mobile part 30 includes an oblong aperture 58 in which the shank of the screw 50 is engaged. Clearly, on screwing the screw 50 into the tapping 54, the head 56 of the screw that is bearing on the upper face 44 of the mobile part 30 causes the mobile part to slide relative to the fixed part, so that its face 42 moves toward the inside wall 38 of the housing 34.

The distal end portion 18 of the spacer body includes a passage 60 enabling free engagement of the median portion 14a of the braid 14, as shown best in FIG. 3. The proximal portion 20 includes two lateral passages 62 and 64 that open onto the external face of the spacer and into the housing 34 and through which the braid 14 passes, as explained later. The opening 48 and the passages 62 and 64 preferably open onto the face of the spacer onto which the housing 34 opens. This facilitates fitting the braid.

In FIG. 3, it is seen that the inside wall 38 of the recess 34 has two portions 66 and 68 inclined to the direction F of movement of the mobile part relative to the fixed part, this direction F of movement being also the direction of insertion of the intervertebral spacer between the vertebrae.

The mobile part 30 also has two inclined faces 70 and 72 conjugate with the faces 66 and 68 of the housing 34. These four inclined faces constitute surfaces for clamping the portions 14b and 14c of the braid 14, those portions 14b and 14c being disposed on either side of the median portion 14a of the braid engaged in the passage 60, of course.

The use of the clamping device conforming to this first mode of use is as follows:

When inserting the spacer between the vertebrae V1 and V2, or more precisely their spinous processes, the mobile part 30 is retracted, i.e. the clamping surfaces 66, 70 and 68, 72 are respectively moved apart to enable free passage of the portions 14b and 14c of the braid. Moreover, the free ends 14d and 14e of the braid are easily accessible because they enter the housing 38 through the slots 62 and 64 and leave it through the opening 48. The slots 62 and 64 and the opening 48 preferably open onto the face of the spacer onto which the housing 34 also opens, which facilitates initial placement of the braid 14. After appropriate traction has been applied to the ends 14d and 14e of the braid, the screw 50 is turned to cause the mobile part 30 to move toward the wall 38 of the housing 34, progressively clamping the portions 14b, 14c of the braid between the clamping surfaces until these two portions of the braid are immobilized relative to the spacer. The head 56 of the screw 50 retains the clamping portion of the mobile part 30.

Moreover, because the median portion 14a of the braid is freely engaged in the passage 60 effective clamping is obtained and therefore effective fixing of the spacer to each of the spinous processes V1 and V2, even with high friction between the braid and one of the spinous processes.

Figure 9:
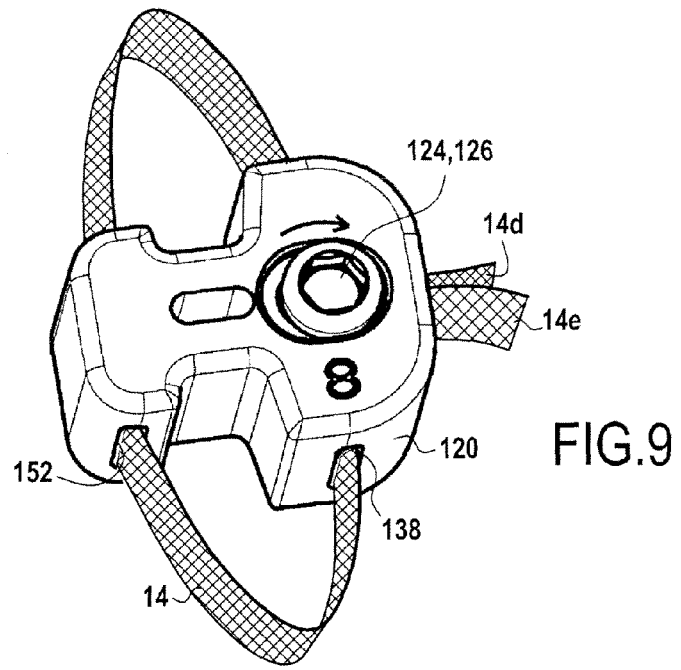
FIG. 9 is a perspective view of a first variant of the first mode of use of the first embodiment of the invention.
Figure 10:
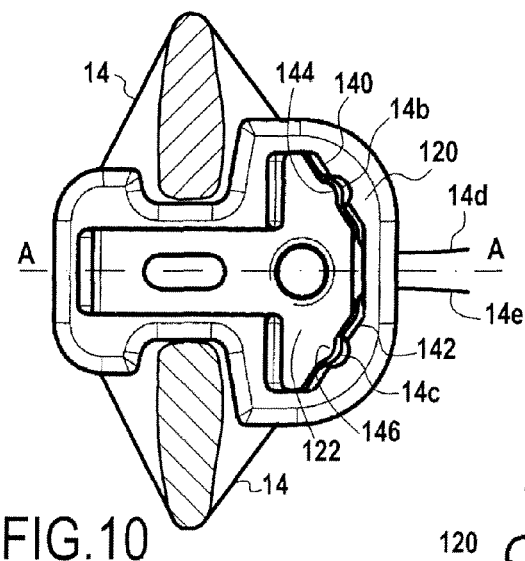
FIG. 10 is a side view of the intervertebral implant shown in FIG. 9.
Figure 10A:
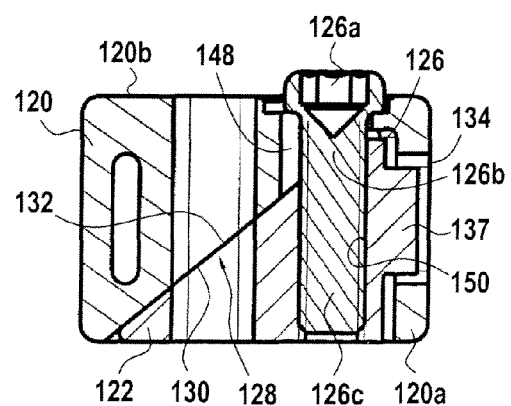
FIG. 10A is a view in section taken along the line A-A in FIG. 10.

A first variant of the clamping device that has just been described is described next with reference to FIGS. 9 and 10.

In this embodiment, the clamping system comprises a fixed part 120 consisting of the body of the spacer, a mobile part 122, and a mechanical displacement member 124 preferably consisting of a screw 126.

The part 120 includes a housing 128 to receive the mobile part 122 opening onto the face 120a. The housing 128 defines an inclined surface 130 that co-operates with the inclined sliding surface 132 of the mobile part 122. Moreover, the proximal end of the fixed part includes an axial opening 134 and two lateral openings 136, which openings can open onto the face 120a of the fixed part 120. The mobile part has at its proximal end an extension 137 adapted to enter the axial opening 134 and two clamping faces 140 and 142 disposed on either side of the extension 137 and preferably inclined to the longitudinal plane of the fixed part. The inside wall of the housing 128 also defines two clamping surfaces 144 and 146 facing the clamping surfaces 140 and 142, respectively, of the fixed part.

The screw 126 has a head 126a bearing on a spot facing on the face 120b of the fixed part 120. The body of the screw 126b passes through an oblong aperture 148 in the fixed part and its threaded part 126c is screwed into tapping 150 formed in the mobile part 122.

The use of the first embodiment is as follows:

The braid 14 is engaged in a slot 152 of the spacer body. It enters the housing 128 through the lateral openings 136. Its portions 14b and 14c to be clamped are disposed between the clamping surfaces 140, 144 and 142, 146, the free ends 14d and 14e of the braid 14 leaving the housing 128 through the axial opening 134. The openings 134 and 138 preferably open onto the face of the spacer onto which the housing 128 also opens.

In the initial position, the mobile part 122 is away from the proximal end of the fixed part 120. The portions 14b and 14c are loose between the clamping surfaces.

When the surgeon has applied the appropriate traction to the free ends 14d and 14e of the braid to clamp the processes V1 and V2 appropriately, the surgeon turns the head 126a of the screw 126. Screwing the screw 126 into the tapping 150 in the mobile part causes the mobile part 122 to move relative to the fixed part 120 in the direction F. This moves the clamping surfaces 144 and 146 toward the surfaces 140 and 142, therefore effectively clamping the portions 14b and 14c of the braid 14.

Referring next to FIGS. 5 to 8, a second mode of use of the first embodiment of the clamping device for the intervertebral implant 10' consisting of the spacer 12' and the braid 14' is described next with reference to FIGS. 5 to 8.

The structure of the intervertebral spacer 10' is identical in terms of its general organization to that of the FIG. 1 spacer 10. The only differences relate to arrangements for constituting the fixed part and the mobile part of the clamping system that carries the general reference 26' in this second embodiment.

Figure 8:
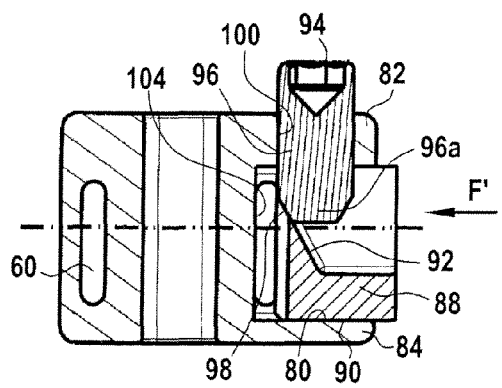
FIG. 8 is a view of the spacer in section on the plane V'-V' in FIG. 6.

As seen better in FIG. 8, a housing 80 is produced in the proximal end portion 20' of the spacer body. This housing has an upper wall 82 and a lower wall 84 that are substantially plane. The end 86 of the housing 80 opens onto the external face of the proximal end portion 20. A mobile part 88 mounted inside the housing 80 so that it can slide therein has a lower sliding face 90 cooperating with the bottom 84 of the housing 80. The upper face of the mobile part 88 defines an inclined surface 92 facing toward the upper wall 82 of the housing 80.

This second embodiment of the clamping device is completed by a mechanical displacement member 94 consisting of a grub screw 96. The lower end 96a of the screw 96 includes a frustoconical portion 98 that can co-operate with the inclined face 92 of the mobile part 88. The screw 96 is engaged in tapping 100 formed in the upper wall 82 of the housing 80. Clearly, when the screw 96 is screwed in, the frustoconical portion 98 co-operates with the inclined portion 92, causing the mobile part 88 to move in the direction F. This moves the internal face 102 of the mobile part 88 toward the face 84 that constitutes the bottom of the housing 80. The inside face 102 of the mobile part 88 preferably includes two projections 106 and 108 forming an edge facing toward the bottom 104 of the housing 80. The proximal portion 20' of the spacer body includes two lateral openings 108 and 110 for the braid 14' to pass through analogous to the openings 62 of the first embodiment. The mobile part 88 includes two lateral flanges 110 and 112 disposed on either side of the inclined portion 92. These lateral flanges 110 and 112 have respective passages 114 and 116 in which the braid 14' passes through them.

Clearly, when the mobile part 88 is moved by the screw 96, sliding relative to the fixed part consisting of the spacer body in the direction of the arrow F, which tends to move the edges 106 and 108 of the mobile part toward the bottom wall 104 of the housing 80, a clamping effect is obtained between the bottom surface 104 of the housing and the edges 106 and 108, thereby clamping the portions 14b and 14c of the braid 14' to immobilize them.

Figure 7:
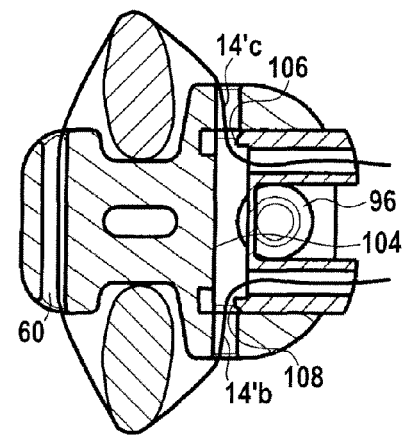
FIG. 7 is a view in section on the plane H'-H' in FIG. 6.
Figure 12:
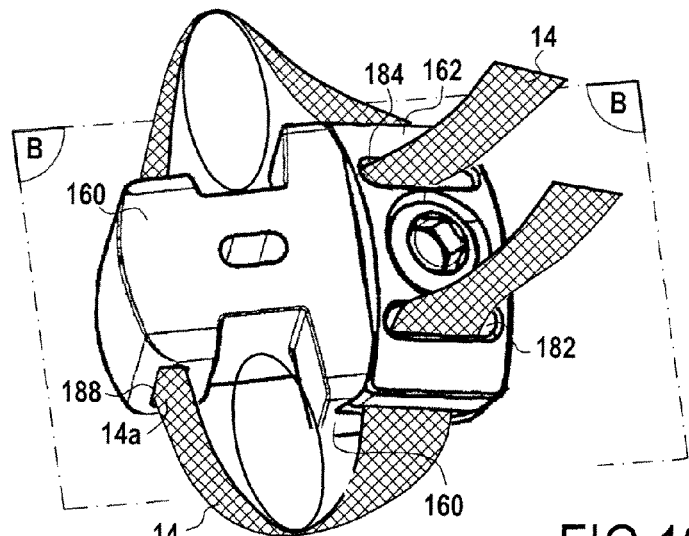
FIG. 12 shows in perspective a second variant of the first mode of use of the first embodiment of the implant.
Figure 13:
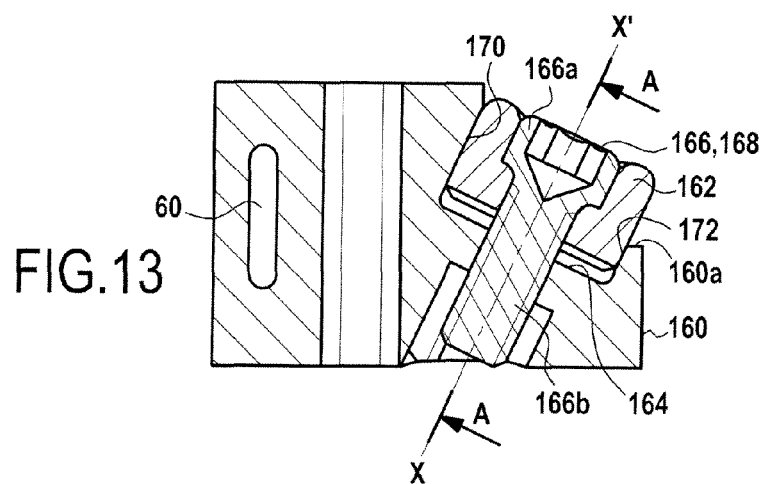
FIG. 13 is a view in longitudinal section on the plane B-B in FIG. 12.
Figure 13A:
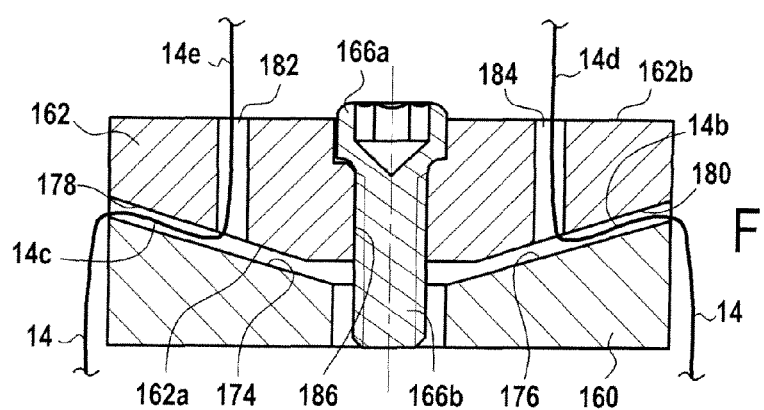
FIG. 13A is a view in section taken along the line A-A in FIG. 13.

A variant of the clamping system represented in FIGS. 6, 7 and 8 is described next with reference to FIGS. 12 and 13.

The clamping system comprises a fixed part 160 consisting of the body of the spacer and a mobile part 162 mounted in a housing 164 formed in the inclined face 160a of the proximal portion of the fixed part. Finally, the clamping system comprises a mechanical member 166 preferably consisting of a screw 168. The mobile part 162 moves in the direction of the axis XX' of the screw 168. It is guided in translation by the parallel faces 170 and 172 of the inside wall of the housing 164, which co-operate with the conjugate faces of the mobile part. The bottom of the housing 164 defines two clamping surfaces 174 and 176 disposed on either side of the screw 166.

The face 162a of the mobile part facing toward the fixed part defines two clamping surfaces 178 and 180 facing the clamping surfaces 174 and 176 of the fixed part 160. This mobile part 162 also includes two slots 182 and 184 that pass completely through it.

The screw 166 has a head 166a that bears in a spot facing on the external face 162b of the mobile part 162 and a threaded portion 166b that co-operates with tapping 186 formed in the fixed part 160.

The braid 14 has a central portion 14a engaged in a slot 188 in the central portion of the spacer.

The braid enters the housing 164 laterally through the gap between the fixed part 160 and the mobile part 162 and its portions 14b and 14c are therefore disposed between the clamping surfaces 174, 178 and 176, 180. The free ends 14d and 14e of the braid emerge from the mobile part 162 through the slots 188 and 184.

When the surgeon has applied suitable traction to the free ends 14d and 14e, the surgeon turns the head 166a of the screw 166 to move the mobile part 162 toward the bottom of the housing 164 in the fixed part. The portions 14b and 14c of the braid are therefore clamped between the clamping surfaces 174 and 180.

It should be emphasized that in all embodiments the member that moves the mobile part relative to the fixed part (spacer body) consists of a screw 50. The heads of the screws are easily accessible to the practitioner after fitting the implant as the heads of these screws open onto the lateral face of the spacer that is accessible to the surgeon.

Moreover, since the clamping device clamps two separate portions of the braid in both circumstances, the median portion 14a, 14'a of the braid is housed inside the spacer body and emerges therefrom only via the ends of the passage 60. This arrangement is much more ergonomic than in the one in which one end of the braid must be fixed to the spacer body by a loop that makes it more difficult to insert the spacer between the spinous processes.

Naturally, it would not go beyond the invention for the braid 14 in the above-described embodiment to have a first end secured to the body of the spacer 12 so that only its second end is clamped by the clamping device. Under such circumstances, the fixed part of the clamping device and the mobile part would naturally each have only one clamping surface.

It is also possible for the braid 14 to be constituted by two braid portions, each having a first end secured to the body of the spacer and a second end clamped by the clamping device.

Figure 11:
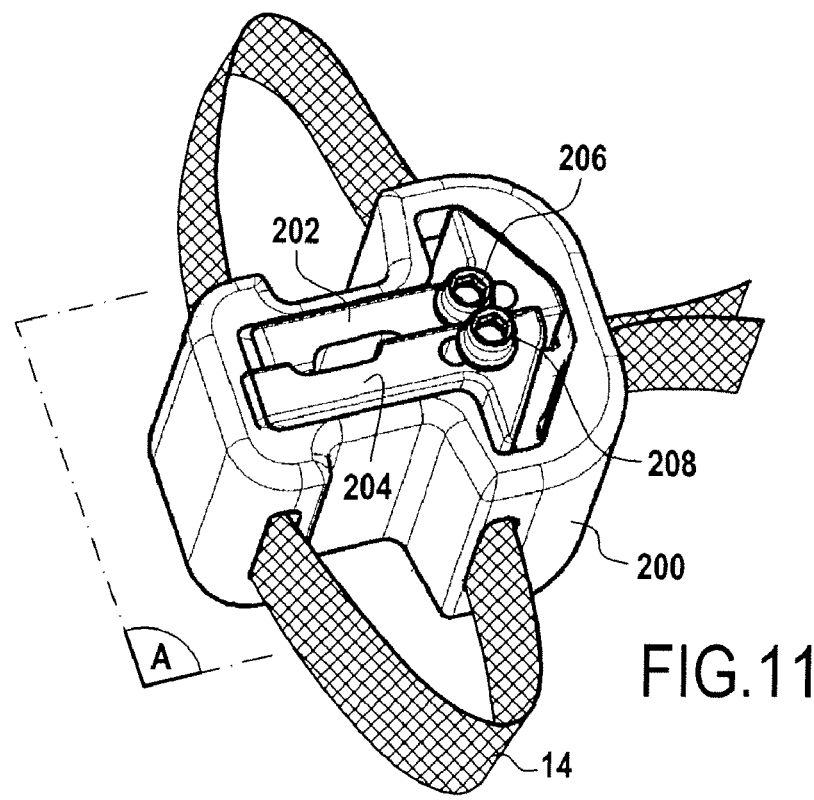
FIG. 11 is a perspective view of an intervertebral implant fitted with a second embodiment of the clamping device.
Figure 11A:
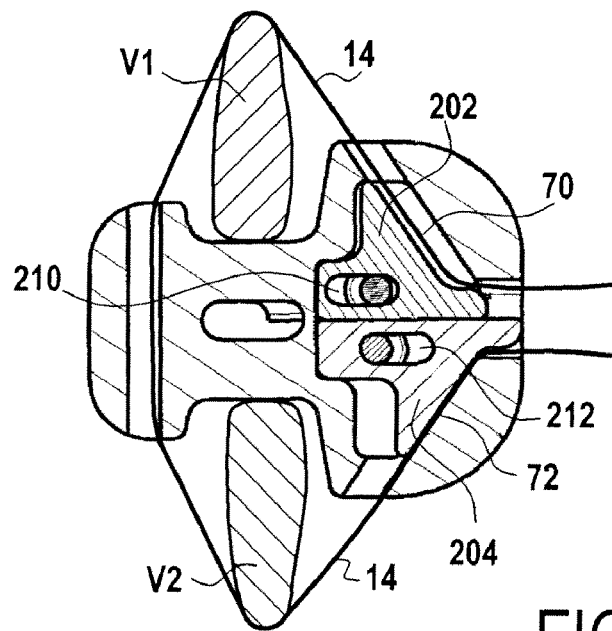
FIG. 11A is a view in section on the plane A-A in FIG. 11.

A second embodiment of the invention, in which the two portions of the braid can be clamped separately, is described next with reference to FIGS. 11 and 11A.

In principle, the mobile portion of the first embodiment is "cut" in two to constitute two mobile parts (each of which mobile parts defines a mobile clamping surface) and the fixed part, which is not modified, defines two separate and fixed clamping surfaces. Each mobile part is associated with a mechanical displacement member which preferably consists of a screw that co-operates with the fixed part and with one mobile part to move the two mobile parts separately and thereby to clamp the two braid portions.

Each of the modes of use described with reference to FIGS. 1 to 4; 5 to 8, 9 and 10, and 12 and 13, respectively, could be modified to replace the single mobile part and the single mechanical displacement member with two mobile parts and two mechanical displacement members.

The modification of the clamping system represented in FIGS. 1 to 4 is described by way of example.

It nevertheless goes without saying that the same modifications could be applied to the other modes of use of the first embodiment.

The clamping device comprises a fixed part 200, consisting of the body 12 of the spacer of the implant that is in every respect identical to that represented in FIGS. 1 to 4. The mobile parts 202 and 204 are each the shape of half of the mobile part 30 in those same figures. The mobile part 202 defines the clamping surface 70 and the part 204 defines the clamping surface 72.

Furthermore, each mobile part 202, 204 is associated with a mechanical displacement member consisting of the respective screws 206, 208, with shanks that pass through the mobile parts by means of a respective oblong hole 210, 212. The corresponding mobile part is moved by turning one of the screws 206 or 208, which therefore clamps the corresponding braid portion, clamping the spacer to one of the spinous processes. To enable separate clamping to each spinous process, the median portion of the braid 14 can be immobilized in the passage 60 in the distal portion of the spacer. It is also possible to use two traction instruments to apply traction to each free end of the braid 14 in succession.

This second embodiment has all the advantages of the first embodiment.

In the above description the intervertebral implants described are especially adapted to lateral insertion. Nevertheless, it would not go beyond the invention if the implant were to have spacers of standard shape for posterior insertion.

It should also be emphasized that in all embodiments the fixed part of the clamping device forms an integral portion of the spacer. This makes the implant easier to fabricate. Nevertheless, it would not go beyond the invention if this first part of the clamping device were to be fitted to the spacer.

The invention claimed is:

1. An intervertebral implant comprising:
   a spacer;
   a braid for fixing said spacer between the spinous processes of two adjacent vertebrae; and
   a clamping device for clamping said braid; wherein said clamping device comprises:
   a fixed first part constituted by a portion of said spacer and defining two distinct first clamping surfaces for clamping said braid;
   a mobile assembly that is mobile relative to said spacer, defining two distinct second clamping surfaces for clamping said braid; and
   displacement means for moving said mobile assembly relative to said fixed part, said displacement means being configured to move said mobile assembly between a first position in which said first and second clamping surfaces face each other but are apart to define two free passages for two distinct portions of the braid, and a second position in which said first and second clamping surfaces are moved towards each other to clamp said two braid portions, said displacement means being further adapted to hold said mobile assembly in its clamping, second position, wherein two braid guiding passages are provided through said first part, said mobile assembly, or both, and wherein said two braid guiding passages are connected to said two free passages and adapted to receive said two braid portions.

2. The intervertebral implant according to claim 1, wherein said first part of the clamping device is an integral portion of said spacer.

3. The intervertebral implant according to claim 1, wherein said spacer comprises a median portion, a proximal end portion, and a distal end portion extending orthogonally relative to the direction in which said spacer is inserted between the vertebrae, said spacer having two recesses disposed respectively at two ends of said median portion between ends of said proximal and distal end portions, the proximal end portion defining at least part of said fixed part of the clamping device.

4. The intervertebral implant according to claim 3, wherein the distal end portion of the spacer includes a passage in which a median portion of said braid is engaged freely.

5. The intervertebral implant according to claim 1, wherein said spacer is configured to enable lateral insertion.

6. The intervertebral implant according to claim 1, wherein said mobile assembly is constituted by a single second part.

7. The intervertebral implant according to claim 6, wherein said displacement means comprise a first sliding face of said first part that is inclined relative to the displacement direction, and a second sliding face of said mobile assembly suitable for co-operating with said first sliding face, said second sliding face also being inclined relative to the displacement direction, and a mechanical displacement member for causing the second sliding face to slide relative to the first sliding face between said first and second positions.

8. The intervertebral implant according to claim 7, wherein said mechanical displacement member is a screw having its threaded end co-operating with tapping formed in the inclined first sliding face of the first part, the shank of the screw passing through said second part via an oblong orifice, and the head of the screw coming into contact with a face of said second part that is opposite from its inclined first sliding face.

9. The intervertebral implant according to claim 7, wherein said mechanical displacement member is a screw having its threaded end co-operating with tapping formed in the inclined second sliding face of said second part, the shank of the screw passing through said first part via an oblong orifice, and the head of the screw coming into contact with a face of said first part that is opposite from its said inclined first sliding face.

10. The intervertebral implant according to claim 6, wherein said displacement means comprise sliding faces parallel to the displacement direction, formed respectively in each of said fixed first part and mobile second part and suitable for co-operating with each other, and a mechanical displacement member.

11. The intervertebral implant according to claim 10, wherein said mechanical displacement member is accessible in one of the lateral faces of the proximal end portion of said spacer.

12. The intervertebral implant according to claim 11, wherein said mechanical displacement member includes an inclined surface formed in said second part and opposite from the sliding face, and a screw engaged in tapping formed in said first part and having one end co-operating with said inclined surface.

13. The intervertebral implant according to claim 11, wherein the mechanical displacement member comprises a screw member of axis parallel to the displacement direction, the head of said screw member bearing against an external face of said mobile second part, the threaded portion of the screw member co-operating with tapping formed in said first part.

14. The intervertebral implant according to claim 1, wherein said mobile assembly comprises two distinct separate mobile second parts, each second part defining one of the two second clamping surfaces.

15. The intervertebral implant according to claim 14, wherein said first part includes a first sliding face, wherein each of said mobile second parts includes a second sliding face, said two second sliding faces being suitable for cooperating with said first sliding face, said intervertebral implant further including two mechanical members for causing the second sliding face of each of said second mobile parts to slide separately relative to said first sliding face of the first part, between said first and second positions.

16. The intervertebral implant according to claim 1, wherein said first and second clamping surfaces are not orthogonal to the displacement direction.

17. The intervertebral implant according to claim 1, wherein said first and second clamping surfaces are in the form of edges.

18. The intervertebral implant according to claim 1, wherein said first and second clamping surfaces include notches, lugs, asperities, or a combination thereof.

* * * * *